US005602097A

United States Patent [19]

Edwards

[11] Patent Number: 5,602,097
[45] Date of Patent: Feb. 11, 1997

[54] SYNTHETIC ANTIBIOTICS

[75] Inventor: David L. Edwards, San Antonio, Tex.

[73] Assignee: Ceres Technologies, Inc., Houston, Tex.

[21] Appl. No.: 305,768

[22] Filed: Sep. 13, 1994

[51] Int. Cl.$^6$ ............... A61K 38/00; C07K 7/00
[52] U.S. Cl. ............... 514/17; 514/18; 530/329; 530/330; 530/331; 424/935
[58] Field of Search .................. 530/329, 330, 530/331; 514/17, 18; 424/93.5

[56] References Cited

U.S. PATENT DOCUMENTS

| | | | |
|---|---|---|---|
| 4,324,683 | 4/1982 | Lim et al. | 252/316 |
| 4,833,092 | 5/1989 | Geysen | 436/501 |
| 5,010,175 | 4/1991 | Rutter et al. | 530/334 |
| 5,182,366 | 1/1993 | Huebner et al. | 530/334 |
| 5,440,016 | 8/1995 | Blondelle et al. | 530/330 |

FOREIGN PATENT DOCUMENTS

| | | | |
|---|---|---|---|
| WO9209300 | 6/1992 | WIPO. | |
| WO94/08010 | 4/1994 | WIPO | C12N 15/29 |

OTHER PUBLICATIONS

Khanashvili et al. (1993) Phe–Met–Arg–Phe–NH2 (FMR-Fa)–related peptides. J. Biol. Chem., 268, 200–205.

Broekaert, W. F. et al., "An Automated Quantitative Assay for Fungal Growth Inhibition," *Fed. Eur. Microbiol. Soc.*, vol. 69, pp. 55–60 (1990).

Broekaert, W. F. et al., "Antimicrobial Peptides from *Amaranthus caudatus* Seeds with Sequence Homology to the Cysteine/Glycine–Rich Domain of Chitin–Binding Proteins," *Biochem.*, vol. 31, pp. 4308–4314 (1992).

Cammue, Bruno P. A. et al., "Isolation and Characterization of a Novel Class of Plant Antimicrobial Peptides from *Mirabilis jalapa* L Seeds," *J. Biol. Chem.*, vol. 267, pp. 2228–2233 (1992).

Janisiewicz, W. J., "Biocontrol of Postharvest Diseases of Apples with Antagonist Mixtures," *Phytopathology*, vol. 78, pp. 194–198 (1988).

Janisiewicz, W. J. et al., "Biological Control of Blue Mold and Gray Mold on Apple and Pear with *Pseudomonas cepacia*," *Phytopathology*, vol. 78, pp. 1697–1700 (1988).

Ohba, Kazunori et al., "Nitropeptin, a New Dipeptide Antibiotic Possessing a Nitro Group," *J. Antibiotics*, vol. XL, pp. 709–713 (1987).

Terras, Franky R. G., et al., "A New Family of Basic Cysteine–rich Plant Antifungal Proteins from *Brassicaeae* Species," *FEBS*, vol. 316, pp. 233–240 (1993).

Sagan, Sandrine, et al., "Differential Contribution of C–Terminal Regions of Dermorphin and Dermenkephalin to Opioid–Sites Selection and Binding Potency," *Biochem. Biophys. Res. Comm.*, vol. 163, pp. 726–732 (1989).

Duchesne, Delphine, et al., "Folding Trends in a Flexible Peptide: Two–dimensional NMR Study of Deltorphin–I, a δ Selective Opioid Heptapeptide," *Biochem. Biophys. Res. Comm.*, vol. 195, pp. 630–636 (1993).

Mor, et al., "Dermorphin and Related Peptides in Rat Tissues," *Neuropeptides*, vol. 13, pp. 51–57 (1989).

Howell, C. R., et al., "Suppression of *Pythium ultimum*–Induced Damping–Off of Cotton Seedlings by *Pseudomonas fluorescens* and its Antibiotic, Pyoluteorin," *Phytopathology*, vol. 70, pp. 712–715 (1980).

Terras, Franky R. G., et al., "Analysis of Two Novel Classes of Plant Antifungal Proteins from Radish (*Raphanus sativis* L.) Seeds," *J. Biol. Chem.*, vol. 267, pp. 15301–15309 (1992).

Janisiewicz, W., et al., "Postharvest Control of Blue Mold and Gray Mold of Apples and Pears by Dip Treatment with Pyrrolnitrin, a Metabolite of *Pseudomonas cepacia*," *Plant Dis.*, vol. 75, pp. 490–494 (1991).

*Primary Examiner*—Christine M. Nucker
*Assistant Examiner*—Benet Prickril
*Attorney, Agent, or Firm*—C. Steven McDaniel, Conley, Rose & Tayon, P.C.; Conley, Rose & Tayon, P.C.

[57] ABSTRACT

Compositions of the current invention are directed toward inhibiting the growth of microorganisms, particularly fungi. The compositions consist of chemically-synthesized antibiotics comprising certain amino acids. Methods of identifying particular antibiotic compositions from libraries of such compositions are disclosed. In addition, methods for preventing microbial growth in plants and animals are disclosed.

28 Claims, No Drawings

SEQUENCE LISTING ( 1 ) GENERAL INFORMATION:

( i i i ) NUMBER OF SEQUENCES: 31

( 2 ) INFORMATION FOR SEQ ID NO: 1:

( i ) SEQUENCE CHARACTERISTICS:
        ( A ) LENGTH: 6 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO: 1:

Xaa  Xaa  Xaa  Xaa  Arg  Phe
    1                          5

( 2 ) INFORMATION FOR SEQ ID NO: 2:

( i ) SEQUENCE CHARACTERISTICS:
        ( A ) LENGTH: 6 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO: 2:

Xaa  Xaa  Xaa  Xaa  Phe  His
    1                          5

( 2 ) INFORMATION FOR SEQ ID NO: 3:

( i ) SEQUENCE CHARACTERISTICS:
        ( A ) LENGTH: 6 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO: 3:

Xaa  Xaa  Xaa  Xaa  Lys  Phe
    1                          5

( 2 ) INFORMATION FOR SEQ ID NO:4:

( i ) SEQUENCE CHARACTERISTICS:
        ( A ) LENGTH: 6 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO: 4:

```
     Xaa  Xaa  Xaa  Xaa  Gln  Arg
     1                 5
```

( 2 ) INFORMATION FOR SEQ ID NO:5:

( i ) SEQUENCE CHARACTERISTICS:
        ( A ) LENGTH: 6 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO: 5:

```
     Xaa  Xaa  Xaa  Xaa  Arg  Met
     1                 5
```

( 2 ) INFORMATION FOR SEQ ID NO:6:

( i ) SEQUENCE CHARACTERISTICS:
        ( A ) LENGTH: 6 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO: 6:

```
     Xaa  Xaa  Xaa  Xaa  His  Met
     1                 5
```

( 2 ) INFORMATION FOR SEQ ID NO: 7:

( i ) SEQUENCE CHARACTERISTICS:
        ( A ) LENGTH: 6 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO: 7:

```
     Xaa  Xaa  Xaa  Xaa  Lys  Leu
     1                 5
```

( 2 ) INFORMATION FOR SEQ ID NO: 8:

( i ) SEQUENCE CHARACTERISTICS:
        ( A ) LENGTH: 6 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO: 8:

```
     Xaa  Xaa  Xaa  Xaa  Arg  Leu
     1                 5
```

( 2 ) INFORMATION FOR SEQ ID NO: 9:

( i ) SEQUENCE CHARACTERISTICS:
        ( A ) LENGTH: 6 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO: 9:

```
Xaa  Xaa  Xaa  Leu  Arg  Phe
  1              5
```

( 2 ) INFORMATION FOR SEQ ID NO: 10:

( i ) SEQUENCE CHARACTERISTICS:
        ( A ) LENGTH: 6 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO: 10:

```
Xaa  Xaa  Xaa  Ile  Arg  Phe
  1              5
```

( 2 ) INFORMATION FOR SEQ ID NO: 11:

( i ) SEQUENCE CHARACTERISTICS:
        ( A ) LENGTH: 6 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO: 11:

```
Xaa  Xaa  Xaa  Phe  Arg  Phe
  1              5
```

( 2 ) INFORMATION FOR SEQ ID NO: 12:

( i ) SEQUENCE CHARACTERISTICS:
        ( A ) LENGTH: 6 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO: 12:

```
Xaa  Xaa  Xaa  Trp  Arg  Phe
  1              5
```

( 2 ) INFORMATION FOR SEQ ID NO: 13:

( i ) SEQUENCE CHARACTERISTICS:
        ( A ) LENGTH: 6 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO: 13:

```
Xaa  Xaa  Xaa  Met  Arg  Phe
  1              5
```

( 2 ) INFORMATION FOR SEQ ID NO: 14:

( i ) SEQUENCE CHARACTERISTICS:
        ( A ) LENGTH: 6 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO: 14:

```
    Xaa Xaa Lys Leu Arg Phe
    1               5
```

(2) INFORMATION FOR SEQ ID NO: 15:

(i) SEQUENCE CHARACTERISTICS:
        (A) LENGTH: 6 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO: 15:

```
    Xaa Xaa Arg Leu Arg Phe
    1               5
```

(2) INFORMATION FOR SEQ ID NO: 16:

(i) SEQUENCE CHARACTERISTICS:
        (A) LENGTH: 6 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO: 16:

```
    Xaa Xaa His Leu Arg Phe
    1               5
```

(2) INFORMATION FOR SEQ ID NO: 17:

(i) SEQUENCE CHARACTERISTICS:
        (A) LENGTH: 6 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO: 17:

```
    Xaa Xaa Thr Leu Arg Phe
    1               5
```

(2) INFORMATION FOR SEQ ID NO: 18:

(i) SEQUENCE CHARACTERISTICS:
        (A) LENGTH: 6 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO: 18:

```
    Xaa Xaa Phe Leu Arg Phe
    1               5
```

(2) INFORMATION FOR SEQ ID NO: 19:

(i) SEQUENCE CHARACTERISTICS:
        (A) LENGTH: 6 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO: 19:

```
Xaa  Xaa  Ser  Leu  Arg  Phe
 1               5
```

( 2 ) INFORMATION FOR SEQ ID NO: 20:

( i ) SEQUENCE CHARACTERISTICS:
        ( A ) LENGTH: 6 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO: 20:

```
Xaa  Xaa  Ile  Leu  Arg  Phe
 1               5
```

( 2 ) INFORMATION FOR SEQ ID NO: 21:

( i ) SEQUENCE CHARACTERISTICS:
        ( A ) LENGTH: 6 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO: 21:

```
Xaa  Xaa  Leu  Leu  Arg  Phe
 1               5
```

( 2 ) INFORMATION FOR SEQ ID NO: 22:

( i ) SEQUENCE CHARACTERISTICS:
        ( A ) LENGTH: 6 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO: 22:

```
Xaa  Xaa  Ala  Leu  Arg  Phe
 1               5
```

( 2 ) INFORMATION FOR SEQ ID NO:23:

( i ) SEQUENCE CHARACTERISTICS:
        ( A ) LENGTH: 6 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO: 23:

```
Xaa  Xaa  Trp  Leu  Arg  Phe
 1               5
```

( 2 ) INFORMATION FOR SEQ ID NO:24:

( i ) SEQUENCE CHARACTERISTICS:
        ( A ) LENGTH: 6 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO: 24:

```
      Xaa  Xaa  Met  Leu  Arg  Phe
      1                  5
```

(2) INFORMATION FOR SEQ ID NO: 25:

(i) SEQUENCE CHARACTERISTICS:
        (A) LENGTH: 3 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO: 25:

```
      Phe  Arg  Phe
      1
```

(2) INFORMATION FOR SEQ ID NO: 26:

(i) SEQUENCE CHARACTERISTICS:
        (A) LENGTH: 3 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO: 26:

```
      Leu  Arg  Phe
      1
```

(2) INFORMATION FOR SEQ ID NO: 27:

(i) SEQUENCE CHARACTERISTICS:
        (A) LENGTH: 3 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO: 27:

```
      Trp  Arg  Phe
      1
```

(2) INFORMATION FOR SEQ ID NO: 28:

(i) SEQUENCE CHARACTERISTICS:
        (A) LENGTH: 3 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO: 28:

```
      His  Arg  Phe
      1
```

(2) INFORMATION FOR SEQ ID NO: 29:

(i) SEQUENCE CHARACTERISTICS:
        (A) LENGTH: 4 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO: 29:

```
    Phe  Leu  Arg  Phe
    1
```

( 2 ) INFORMATION FOR SEQ ID NO:30:

( i ) SEQUENCE CHARACTERISTICS:
        ( A ) LENGTH: 4 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO: 30:

```
    Trp  Leu  Arg  Phe
    1
```

( 2 ) INFORMATION FOR SEQ ID NO: 31:

( i ) SEQUENCE CHARACTERISTICS:
        ( A ) LENGTH: 5 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO: 31:

```
    Phe  His  Leu  Arg  Phe
    1                    5
```

SYNTHETIC ANTIBIOTICS

BACKGROUND OF THE INVENTION

A. Field of the Invention

The invention relates to synthetic chemical compositions and methods of testing such compositions to determine which of such compositions inhibit fungal growth. The compositions of the invention may be used to prevent, limit, or otherwise treat fungal damage to agricultural and horticultural crops, particularly to seeds, seedlings and agricultural commodities, including mature plants such as trees. Certain of the compositions and methods of the invention may be used to treat non-plant fungal diseases, such as those of animals including man. The compositions of the invention are especially useful where conditions are conducive to fungal disease development and where control of fungal growth is preferably accomplished with compositions which are not toxic to non-fungal cells.

B. Description of the Related Art

A common problem in agriculture is the reduced yield and crop failure that is caused by plant pathogenic microorganisms. For example, in Texas, diseases of rice, soybeans, and cotton caused by plant pathogenic microorganisms reduced state yields by an estimated 15%, 13%, and 27% in 1992, respectively. In addition to field crop losses, disease losses to horticultural plants and forest trees also occurs. Post-harvest fungal contamination may also lead to reduction in yields and the post-harvest values of plant produce. Current strategies for the control of disease include planting of resistant cultivars and use of known pesticides and fungicides.

Unfortunately, many of the most effective antifungal chemicals show undesirable persistence in the environment. In other instances, such chemicals have low specificity as to the target organism. Where non-target organisms are affected by such low specificity chemicals, it is not uncommon to observe undesired biological activity, including human toxicity (teratogenicity, mutagenicity, carcinogenicity, etc.). Public concerns over the use of foreign chemicals in the environment provide a powerful incentive for developing alternative methods of fungal control.

Common agricultural fungal infections include both vascular and non-vascular diseases. Where the diseases are nonvascular, conditions such as damping off and root rot may occur. Damping off (a symptom of pathogenic attack of seed tissue, e.g., fungal attack) occurs as a result of damage to seeds and seedling roots during germination, either before or after emergence from the soil. Seeds experiencing damping off fail to germinate, become soft, shrink, and finally disintegrate. Post-emergence root rot due to pathogen infection of plant tissue is also responsible for large decreases in the viability of cultivated plants.

Control of damping off and root rot has been attempted by breeding resistant plants with variable success. However, completely resistant cultivars have not been developed and microbial diseases remain a major cause of crop loss. This loss is especially evident in wet growth environments or where crops are repeatedly planted in the same fields. Improved cultural practices, while of some value, similarly fail to provide sufficient relief.

For instance, bananas (family Musaceae) are the most important tropical fruit in the world with more than 62 million tons (if plantains are included) produced annually. For adequate growth of these large perennial herbs, a constant high moisture and tropical temperature are required (16°–35° C.). These same conditions are also highly conducive to the major diseases of banana-panama disease, Sigatoka disease, black leaf streak/black Sigatoka, Moko disease, blackhead, and banana bunchy top virus. Panama disease is caused by *Fusarium oxysporum* f.sp. cubense (races 1, 2, and 4). Black leaf streak/black Sigatoka is caused by *Mycosphaerella fijiensis*. Moko disease is caused by *Pseudomonas solanacearum*.

Biological control of fungal diseases in plants has been the subject of prior investigation. See for example, related U.S. Pat. Nos. 4,942,032 and 4,906,611. These patents disclose the production and use of a naturally-occurring antifungal product ("AFP") produced from Pediococcus species to control post-harvest diseases including mucor rot, gray mold, and blue mold in fruit. U.S. Pat. No. 5,244,680 discloses the use of various species of Cryptococcus to prevent postharvest spoilage of fruit. U.S. Pat. No. 5,049,379 discloses the use of a fungicide isolated from *Bacillus cereus* or use of the organism itself to control infection of certain legumes by *Phytophthora megasperma* f. sp. medicaginis and *Phytophthora megasperma* f. sp. glycinea. The use of microbial agonists to inhibit the growth of pathogenic fungi, however, has severe limitations. The antagonistic effects of the control agent are dependent upon the establishment and growth of that agent in the particular ecological niche in which the pathogen is found. Both abiotic and biotic factors can affect such establishment and subsequent growth of the antagonistic microorganism which in turn affects the production of the anti-fungal agent.

Other research has been directed to the isolation of naturally-occurring antifungal compounds from Pseudomonas species. An isolate from Pseudomonas, L-22-64, and yeast, F-43-31, is able to control blue mold on apples. W. J. Janisiewicz, Phytopathology 78:194–198 (1988). The antifungal agent has been identified as pyrrolnitrin. W. J. Janisiewicz and J. Poitmann, Phytopathology 78:1697–1700 (1988). Other examples of naturally-produced compounds which have antifungal activity include: phenazine, phloroglucinol and pyoluteorin. In many cases, the active component of the natural antifungal agents has not been identified nor completely characterized. Since many of these naturally-produced, antifungal agents are poorly characterized at best, the persistence and toxicity of these compounds in the environment is unknown. Furthermore, the fact that these compounds are produced by microbes in the environment suggests that they may have a limited spectrum of antimicrobial activity.

Peptides are effectors of a variety of physiological processes and can act as antimicrobials inhibiting the growth of fungi and other microbial cells. Several cysteine-rich antifungal peptides have been isolated from radish seeds. These peptides, which range in length from 23 to 30 amino acids, have various antifungal activities against *Alternaria brasicola, Botrytis cinerea, Fusarium culmorum, Pyricularia oryzae, Fusarium oxysporum*, and *Verticillium dahliae*. Terras et at., *FEBS Letters* 316, 233 (1993); Terras et al. *J. Biol. Chem.* 267, 15301 (1992). Cysteine-rich peptides have also been isolated from the seeds of *Mirabilis jalapa*. These peptides have antifungal activity against *Alternaria brasicola, Ascochyta pisi, Botrytis cinerea, Cercospora beticola, Colletotrichum lindemuthianum, Fusarium culmorum, Fusarium oxysporum, Nectria haematocca, Phoma betea, Pyrenophora tritici-repentis, Pyricularia oryzae, Rhizoctonia solani, Verticillium dahliae* and *Venturia inaequalis*. The peptides also inhibited growth of several Gram-positive bacteria. B.P.A. Cammue, *J. of Biol. Chem.* 267, 2228 (1992). Other cysteine-rich peptides have been isolated from the seeds of *Amaranthus caudatus*. W. F. Broekaert et at., *Biochemistry* 31, 4308 (1992). However, the cysteine content of these peptides if produced synthetically will likely result in polymerization of the monomer peptide into aggregates of two or more monomers. These aggregates have unknown anti-fungal activity. Thus, aggregate formation can result in variable levels of activity and specificity.

Other naturally-occurring antifungal peptides have been characterized to a greater degree. A derivative of a dipeptide ("nitropeptin") has been isolated with growth-inhibitory activity against *Pyricularia oryzae*. The dipeptide was purified from *Streptomyces xanthochromogenus*. K. Ohba et al., *The Journal of Antibiotics* 40, 709–713 (1986). Nitropeptin is thought to be a competitive inhibitor of glutamic acid metabolism in protein synthesis. As such, it is not likely to be an effective antimicrobial in nutrient-rich growing conditions or in organisms with glutamic acid biosynthetic capabilities. A naturally-derived cyclic decapeptide, calophycin, also has been shown to exhibit antimicrobial properties. S.-S. Moon, *J. Org. Chem.* 57, 1097 (1992). The peptide was found to contain several modified amino acids including a D-aspartic acid residue and an N-methyl asparagine residue and a fatty acid residue [(2R, 3R, 4S)-3-amino-2-hydroxy-4-methylpalmitic acid]. However, cyclic peptides are difficult to synthesize in high purity and/or at high recovery rates due to the cyclization chemistry. In addition, *Bacillus subtilis* antifungal peptides have been demonstrated to control brown rot in peaches. C. G. Guelderner et al., *Journal of Agricultural and Food Chemistry* 36:366–370 (1988). Naturally-occurring peptides such as nisin as well as naturally-occurring antibiotic acids such as propionic acid have been used in food preservation. However, the environmental stability and toxicities of these naturally-occurring compounds are generally unknown. Furthermore, where such antifungal agents are derived from natural sources, only one or the other stereoisomer will typically demonstrate the desired antifungal activity.

The use of natural antifungal products isolated in commercial quantity from microorganisms is limited in usefulness due in large part to purification problems. Large scale cell culture of the antifungal agent producing microorganism is required for the purification of the antifungal product. In many instances, the cultural isolate responsible for the production of the antifungal agent is not an isolate which is easily batch-cultured or it is entirely incapable of batch culturing (e.g., obligate pathogens). Furthermore, complicated purification strategies are often required to purify the active product to a reasonable level of homogeneity. A substantial disadvantage to the use of naturally-derived antifungal agents is the potential for co-purification of unwanted microbial byproducts, especially byproducts which are undesirably toxic. In many cases, these factors lead to high production costs and make large scale isolation of antifungal products from natural isolates impractical. Purifications may be even more difficult where racemized mixtures are possible where only a single stereoisomer is active, or where disulfide linkages are possible between peptide monomers.

The search for antimicrobial products for agricultural use has lagged behind the search for such products in human medicine. For instance, synthetic peptides have emerged as useful research tools in the development of vaccines in biomedical research. Pinilla, C., et al. *Vaccines* 92,25 (1992). Such peptides have been used to resolve details of antigen-antibody interactions (Lerner, R. A. *Nature* 299,592 (1982)), to map protein products of brain-specific genes (Gramsch, C., et al. *Neurochem.* 40:1220 (1983)), and to prepare optimal analogs of biologically active peptides (Cull, M. G., et al. *Proc. Natl. Acad. Sci.* USA 89,865 (1992)), Furka, A., et al. *Int. J. Pept. Protein Res.* 37:487 (1991)) and in microdilution assays for the development of novel antimicrobial peptides (against *S. aureus, P. aeruginosa, C. albicans*) (Houghten, et al. 1991; Houghten, et al. 1992a).

U.S. Pat. No. 5,254,535 incorporated herein by reference, discloses the use of peptides and peptide derivatives to potentiate the effects of antibiotics used in standard antimicrobial therapies. The peptides used were 14–50 residues in length, requisitely amphiphilic in nature and are predicted to have ion channel-forming characteristics. It is suggested that these peptides may operate to destabilize cell membranes. The peptides disclosed are composed of tetrameric sequences of defined motifs. The motif includes two adjacent hydrophobic residues and at least one basic residue while the remaining residue may be either basic or neutral. The hydrophobic residues am requisitely located together. While the modes of action of certain peptides have been determined (see, e.g., Fiedler et al. 1982; Isono and Suzuki 1979), mechanisms which explain the mode of action and specificity of such peptides have typically not been determined. Where such studies have been conducted in fungal research, initial studies to determine antifungal mode of action of peptides involved a physical examination of mycelia and cells to determine if the peptides could perturb membrane functions responsible for osmotic balance, as has been observed for other peptides (Zasloff, M. 1987. *Proc. Natl. Acad. Sci.* USA 84:5449–5453). Other potential modes of action could include disruptions of macromolecular synthesis or metabolism.

U.S. Pat. No. 5,126,257 discloses the isolation and use of a naturally-occurring peptide derived from lysed human polymorphonuclear leukocyte extracts. The active agent kills Gram-positive and Gram-negative bacteria. However, its activity against fungi is not known. U.S. Pat. No. 4,725,576 discloses the use of peptides to fight fungal infections. The peptides contain at least 14% histidine. Histidine hexamers are specifically disclosed that control *Candida albicans* and *Streptococcus mutans* infections.

Recently developed methods permit the preparation of synthetic peptide combinatorial libraries ("SPCLs") that are composed of equimolar mixtures of free peptides that can be used with in vitro methods to determine bioactivity (Furka, A., et al. *Int. J. Pept. Protein Res.* 37:487 (1991), Houghten, R. A., et al. *Nature* 354:84 (1991), Houghten, R. A., et at. *BioTechniques* 13:412 (1992). Libraries can consist of D-or L- amino acid stereoisomers or combinations of L- and D- and/or non-naturally-occurring amino acids. Other methods for synthesizing peptides of defined sequence are also known. Similarly, large scale preparative methods are known. Certain recombinant methods for producing peptides are also known. See, e.g., U.S. Pat. No. 4,935,351.

Current compositions for controlling fungal pathogen infections have limited use because of their low specificity, human toxicity and persistence in the environment. Even so, due to the inability to sufficiently control fungal growth through breeding resistance and cultural practices, it is necessary to find antifungal agents which do not have such undesirable characteristics. The use of microbes to control fungus growth in the environment is difficult. The use of natural antifungal products isolated in commercial quantity from microorganisms is also limited in usefulness due in large part to purification problems, especially when having to purify racemized mixtures. Moreover, searching for naturally-produced antifungal agents is a very time-consuming process with a very low-probability of success. Even where such naturally-occurring peptides are located, synthesis of the peptide may be problematic (e.g., disulfide formation, high histidine requirements, etc.). Methods and compositions are needed which will provide a means of easily synthesizing and testing for antifungal compositions which do not suffer from the same limitations as naturally-occurring peptides.

SUMMARY OF THE INVENTION

The present invention overcomes disadvantages of previously known fungicides in that the compositions of the invention are chemically defined species that are easily synthesized and purified. They are not dependent upon the genetic stability or growth properties of microorganisms for their production. Antimicrobial treatment using the compositions and methods of the invention does not require contacting an agricultural commodity with unpredictable, live microbes. Moreover, the methods and compositions of the present invention provide an array of different antibiotic compounds which are shown to have particular effectiveness in treating fungal diseases of plants and animals.

The compositions of the invention are effective in controlling fungal pathogen infections and yet demonstrate a high degree of specificity to the target fungi, low toxicity and controlled persistence in the environment. Using the methods of the invention, it is possible to produce antifungal agents in a much shorter time and with a considerably higher-probability of success than screening natural isolates for such activity. Since the methods of the invention can control the chemical nature of the antifungal agents thus produced, synthesis and purification of the peptides is much less problematic (e.g., cysteine is eliminated).

Compositions of this invention comprise peptides of known chemical structure and characteristics. The use of D-amino acids increases the stability of certain of these compounds by being insensitive to common biological degradation pathways that degrade L-amino acid peptides. For instance, L-amino acid peptides may be stabilized by addition of D-amino acids at one or both of the peptide termini. However, biochemical pathways are available which will degrade even D-amino acids in these peptides so that long term environmental persistence is not a problem. Of course, where the compositions of the invention act rapidly or need not otherwise be stabilized, L-amino acids or mixtures of L-and D- amino acids may be useful. Unlike antifungal agents which only work as one or another stereoisomer, the compositions of the invention work well as either one or another stereoisomer or as a mixed stereoisomeric composition.

Research leading to the current invention evaluated SPCLs for activity against fungal pathogens, including pathogens of plants as well as those of animals. The library was composed of 52,128,400 six-residue peptides, each peptide being composed of D-amino acids and having non-acetylated N-termini and amidated C-termini. An iterative process was used to identify active peptide sequences with broad spectrum antifungal activity. The method used a hexapeptide library with the first two amino acids in each peptide chain individually and specifically defined and with the last four amino acids consisting of equimolar mixtures of 20 amino acids. Four hundred (400) ($20^2$) different peptide mixtures each consisting of 130,321 ($19^4$)(cysteine was eliminated) individual hexamers were evaluated. In such a peptide mixture, the final concentration for each peptide was 9.38 ng/ml, in a mixture composed of 1.5 mg (peptide mix)/ml solution. This mixture profile assumed that an average peptide has a molecular weight of 785. This concentration was sufficient to permit bioactivity testing. Subsequently, both D- and L- amino acid containing peptides were constructed and tested.

The invention discloses peptide compositions that can control fungal pathogens, primarily those of plants. The compositions of the invention comprise a mixture of peptides derived from amino acids that are between 3 to 25 residues in length (a length readily accomplished using standard peptide synthesis procedures), preferably six residues in length. Other compositions of the invention include substantially homogeneous peptide compositions useful as antimicrobial agents. Further compositions of interest in the invention include peptide compositions formulated for use such as those contained in microspheres.

The peptides of the invention may be constructed using a variety of amino acid precursors. Of course, the peptides may be homogenous compositions containing only D-, L- or cyclic (non-racemic) amino acids. The chemical structure of such amino acids (which term is used herein to include imino acids), regardless of stereoisomeric configuration, may be based upon that of the nineteen or twenty naturally-occurring amino acids: alanine (Ala; A), arginine (Arg; R), asparagine (Asn; N), aspartate (Asp; D), glutamine (Gln; Q), glutamate (Glu; E), glycine (Gly; G), histidine (His; H), isoleucine (Ile; I), leucine (Leu; L), lysine (Lys; K), methionine (Met; M), proline (Pro; P), phenylalanine (Phe; F), serine (Ser; S), threonine (Thr; T), tryptophan (Trp; W), tyrosine Tyr; Y), and valine (Val; V). Cysteine (Cys; C) is excluded to prevent disulfide linkage problems in the products. The compositions of the invention may also be non-homogenous, containing for instance both D-, L- and/or cyclic amino acids. The peptide compositions may also contain amino acids which are other than the naturally-occurring amino acids, such as norleucine, etc.

More specifically, the compositions of the invention will be one of the group of peptides disclosed in Sequence ID Nos. 1–31. These sequences establish a number of precise chemical compositions which have been shown to have antifungal activity against a spectrum of fungi. In certain instances, the peptides of the invention as shown in the Sequence IDs will have completely defined sequences. In other instances, the sequence of the antifungal peptide will be defined for only certain of the C-terminal amino acid residues leaving the remaining amino acid residues defined as equimolar ratios. Thus, in each aliquot of the SPCL containing a given Sequence ID No. containing a variable residue, the variable residues will each be uniformly represented in equimolar amounts by one of nineteen different naturally-occurring amino acids in one or the other stereoisomeric form. However, the variable residues may be rapidly defined using the methods of the invention for determining the most effective peptides for controlling fungal growth.

Thus, it can be seen in the Examples that follow that the C-terminal sequence "FRXXXX" (Seq. ID No. 1) exhibited antifungal activity for a wide spectrum of fungi. For ease of reference, peptides herein are routinely written in a C-terminal to N-terminal direction to denote the sequence of synthesis. However, the conventional N-terminal to C-terminal manner of reporting amino acid sequences is utilized in the Sequence Listings. This relatively variable composition, therefore, can be described as an antibiotic composition of the invention even though it is likely that not every component of the mixed peptide composition possess antibiotic activity. In the next round of identification of antibiotic peptide compositions based upon the "FRXXXX" (Seq. ID No. 1) parent composition of known antibiotic activity, "FRLXXX" (Seq. ID No. 9) peptide compositions were found to exhibit significant antibiotic activity. Similarly to the parent composition of "FRXXXX" (Seq. ID No. 1), the "FRLXXX" (Seq. ID No. 9) peptide composition will have a mixed equimolar array of peptides representing the same nineteen amino acid residues, some of which may have antibiotic activity and some of which may not have such activity. Overall, however, the "FRLXXX" (Seq. ID No. 9) peptide composition is itself an antibiotic composition of the invention. This process may be carried out to the point where completely defined peptides are produced and tested by the methods of the invention for their antibiotic activity. In those instances, as for example was accomplished for "FRLHF" (Seq. ID No. 31), all amino acid residues in a six residue peptide will be known.

However, it is not necessary for a peptide composition of demonstrable antibiotic activity to be completely defined as to each residue. In fact, in certain instances, especially where the peptide compositions of the invention are being used to treat an array of fungal diseases each with a different causative agent, mixed peptide compositions will be preferred. This is also likely to be the case where there is a desire to treat a fungal disease with lower concentrations of numerous antibiotics rather than a higher concentration of a single chemical composition. In other instances where, for instance, due to the increased cost of testing or producing a completely defined peptide antibiotic is prohibitive, the mixed peptide compositions of the invention having one or more variable amino acid residues may be preferred. Thus, antibiotic compositions comprising equimolar mixture of peptides produced in a synthetic peptide combinatorial library utilizing the methods of the invention have been derived and shown to have desirable antibiotic activity. These relatively variable compositions are specifically those based upon the sequence of one of the peptides of Seq. ID Nos. 1–24.

The antibiotic compositions of the invention may also comprise a carrier. In certain instances, the carrier will be one suitable for pharmaceutical applications. In other instances, the carrier will be one suitable for use in applying the antibiotic compositions onto plants. In either instance, the carder selected must be a carrier whose chemical and/or physical characteristics do not significantly interfere with the antibiotic activity of the peptide composition. It is known, for instance that certain microsphere carriers may be effectively utilized with proteinaceous compositions in order to deliver these compositions to a site of preferred activity such as onto a topical surface of a plant or animal. Liposomes have been similarly utilized to deliver labile antibiotics by injection or inhalation to internal sites within an organism. Saline solutions, pharmaceutically acceptable buffers and solvents and the like may also be utilized as carriers for the peptide compositions of the invention.

The antibiotic compositions consisting essentially of one of the peptides of Seq. ID Nos. 25–31 have no variable residues. These compositions have been demonstrated to inhibit the growth of fungal cells from fungi selected from the group of pathogenic fungi consisting of Fusarium, Rhizoctonia, Ceratocystis, Pythium, Mycosphaerella and Candida species.

Similarly, processes for inhibiting growth of fungal cells comprising contacting the fungal cell with an antibiotic composition comprising at least one of the peptides of Seq. ID Nos. 1–31 are described. Using the techniques of the invention, selected pathogenic fungi, some pathogens of plants and others pathogens of animals, have been tested. The processes of the invention have, therefore, been specifically shown to be effective where the fungal cell is a fungal cell selected from the group of fungi consisting of Fusarium, Rhizoctonia, Ceratocystis, Pythium, Mycosphaerella and Candida species.

The processes of the invention can be applied to fungal cells which are those of a pathogen of a plant. In certain preferred instances, the plant portion or organ which will be treated is a seed of the susceptible plant organism. In others, the processes of the invention are applied to fungal cells of a pathogen of an animal, such as a human.

A method for selecting antibiotic compositions is also described. The method comprises first creating a synthetic peptide combinatorial library as described herein. Next, as further described in detail herein, a step of contacting a battery of fungal cells with aliquots of the synthetic peptide combinatorial library, each of which aliquots represents an equimolar mixture of peptides in which at least the two C-terminal amino acid residues are known and which residues are in common for each peptide in said mixture is accomplished. After allowing an appropriate period for growth, a next step is accomplished in which the growth of the battery of fungal cells as compared to untreated control cells is measured. Lastly, a determination is made of which of the aliquots most reduces the growth of fungal cells overall in the battery of fungal cells.

Of course, the same method may be carried out in which each of the aliquots represents an equimolar mixture of peptides in which at least three, four, five or more C-terminal amino acid residues are known (depending upon the overall length of the ultimate peptide in the SPCL). Typically, such increasingly defined aliquots will be sequentially tested in order to select the succeeding best candidate peptides for testing. Thus, an additional step in the method entails utilizing the determination of which of the aliquots reduces the growth of fungal cells overall in said battery of fungal cells to select which aliquots to next test of a synthetic peptide combinatorial library where at least one additional C-terminal amino acid residue is known.

A method of treating a fungal disease is also disclosed. The method comprises first creating a synthetic peptide combinatorial library and contacting aliquots of the synthetic peptide combinatorial library with a cell of a fungus believed to be the causative agent of the disease. Next, a process of selecting those aliquots of the synthetic peptide combinatorial library which most reduce the growth of the fungal cell is carried out. Ultimately, the disease is treated in an organism susceptible to the disease by application of the aliquot of the synthetic peptide combinatorial library which most reduces the growth of the causative agent's cells. The treatment step may comprise topical application to the susceptible organism such as topical creams and ointments in the case of animals, or as sprays, fogs, mists, powders and the like in the case of plants. In other instances, it will be preferred to treat the susceptible organism with oral, nasal, gavage, enema, suppository or other internal application. In others instances, the treatment step will comprise application by injection.

It will be recognized, by those of skill in the art, that the peptides of the invention once selected may be modified to contain functionally equivalent amino acid substitutions and yet retain the same or similar antifungal characteristics. The importance of the hydropathic index of amino acids in conferring biological function on a protein has been discussed generally by Kyte and Doolittle (1982). It has been found by these researchers and others that certain amino acids may be substituted for other amino acids having a similar hydropathic index or score and still retain similar if not identical biological activity. As displayed in Table I below, amino acids are assigned a hydropathic index on the basis of their hydrophobicity and charge characteristics. It is believed that the relative hydropathic character of the amino acid determines the secondary structure of the resultant protein, which in turn defines the interaction of the protein with the substrate molecule. Similarly, in peptides whose secondary structure is not a principal aspect of the interaction of the peptide, position within the peptide and the characteristic of the amino acid residue determine the interactions the peptide has in a biological system. It is proposed that biological functional equivalence may typically be maintained where amino acids having no more than a ±1 to 2 difference in the index value, and more preferably within a ±1 difference, are exchanged.

TABLE I

| AMINO ACID | HYDROPATHIC INDEX |
|---|---|
| Isoleucine | 4.5 |
| Valine | 4.2 |
| Leucine | 3.8 |

TABLE I-continued

| AMINO ACID | HYDROPATHIC INDEX |
| --- | --- |
| Phenylalanine | 2.8 |
| Cysteine/Cystine | 2.5 |
| Methionine | 1.9 |
| Alanine | 1.8 |
| Glycine | −0.4 |
| Threonine | −0.7 |
| Tryptophan | −0.9 |
| Serine | −0.8 |
| Tyrosine | −1.3 |
| Proline | −1.6 |
| Histidine | −3.2 |
| Glutamic Acid | −3.5 |
| Glutamine | −3.5 |
| Aspartic Acid | −3.5 |
| Asparagine | −3.5 |
| Lysine | −3.9 |
| Arginine | −4.5 |

Thus, for example, isoleucine, which has a hydropathic index of +4.5, can be substituted for valine (+4.2) or leucine (+3.8), and still obtain a protein having similar biologic activity. Alternatively, at the other end of the scale, lysine (−3.9) can be substituted for arginine (−4.5), and so on.

Accordingly, these amino acid substitutions are generally based on the relative similarity of R-group substituents, for example, in terms of size, electrophilic character, charge, and the like. In general, although these are not the only such substitutions, the preferred substitutions which take various of the foregoing characteristics into consideration include the following:

TABLE II

| Originally Screened Residue | Exemplary Substitutions |
| --- | --- |
| alanine | gly; ser |
| arginine | lys |
| asparagine | gln; his |
| aspartate | glu |
| cysteine | ser |
| glutamate | asp |
| glutamine | asn |
| glycine | ala |
| histidine | asn; gln |
| isoleucine | leu; val |
| leucine | ile; val |
| lysine | arg; gln; glu |
| methionine | met; leu; tyr |
| serine | thr |
| threonine | ser |
| tryptophan | tyr |
| tyrosine | trp; phe |
| valine | ile; leu |

Homogeneous peptide compositions are chiefly composed of a single active peptide species of a well-defined sequence. Minor amounts (less than 20% by moles) of impurities may coexist with the peptide in these compositions so long as they do not interfere with the growth inhibitory properties of the active compound.

For the purposes of this invention, "active ingredient" refers to the peptide with the ability to inhibit the growth of target microorganisms. Target microorganisms include but are not limited to those fungi that cause root rot, damping off, systemic infections, vascular diseases, and infections of certain surface areas of plants. The target microorganism may also include pathogens of animals and man, such as yeast infections common in certain disease states of man.

This invention further provides a method of inhibiting microbial growth in plants with the peptide compositions of the invention. Fungal infections can be prevented at various stages of crop development including: protection of seeds and seed sprouts, growth of seedlings and plants, protection of harvested produce, and commodity storage. The method comprises coating plant part or organ with the peptide compositions of the invention in a coating mixture comprising a noninterfering carder and an effective quantity of the antimicrobial composition. Alternatively, the antimicrobial composition may be mixed with a noninterfering liquid carrier and contacted with seeds, seedlings, plants or harvested produce or may be introduced systemically into plants.

DESCRIPTION OF PREFERRED EMBODIMENTS

Example I

Synthesis of an SPCL

Methods of constructing peptides of defined or at least partially defined sequences, which peptides may then be selected for biological activity, are known (i.e., U.S. Pat. Nos. 4,833,092, 5,182,366, 5,010,175, and Geysen, Proc. Ntl. Acad. Sci. USA 81:3998–4002). These methods are incorporated specifically herein to the extent that they provide suitable alternative methods for synthesizing such peptides. The techniques which have been found in the present invention to be suitable for synthesizing the peptide compositions of the invention are generally those of Houghten et al. Biotechniques 4:522–524 (1986) and Houghten, Proc. Ntl. Acad. Sci. USA 82:5131–5135 (1985), both of which references are specifically incorporated herein to the extent they provide supplemental materials and methods.

Fmoc (9-Fluorenylmethoxycarbonyl) chemistry was used in the production of the peptide libraries. This approach was used with all peptides of the invention whether they comprised D- or L- analogs. Unless otherwise indicated, the specific peptides described further herein comprise D-analog sequences. The Fmoc moiety protects the N-alpha-amino groups of the amino acid derivatives and can be removed by base such as piperidine, whereas the side chain functional groups are protected by acid-sensitive protecting groups. The first amino acid is added to an acid sensitive linker attached to a polystyrene resin. Successive amino acids are attached via a cycle of Fmoc removal with 20–25% piperidine in DMF:NMP (9:1; the NMP is added to help solvate the resin, which improves Fmoc removal), washing of the resin 6× with DMF, and addition of the next Fmoc protected amino acid along with an appropriate coupling agent such as PyBOP (Benzotriazole-1-yl-oxy-trix-pyrrolidino-phosphonium hexafluorophosphate, the noncarcinogenic analogue of BOP), HBTU (2-(1H-Benzotriazole-1-yl)-1,1,3,3-tetramethyluronium hexafluorophosphate), of DCCl (N,N'-Dicyclohexylcarbodiimide), along with a base such as N-methylmorpholine or Diisopropylethylamine and HOBT (N-hydroxylbenzotriazole), which reduces racemization during coupling. For small peptides (<10 amino acids), a single coupling step is usually sufficient, with a 3-8 amino acid excess depending on the peptide synthesis equipment used along with a similar excess of each of the above chemicals.

For long or complicated peptides, the above reactants can be removed after coupling is allowed to proceed for 20 to 45 mins, at which time rather than wash the resin with DMF and remove the Fmoc for the next amino acid cycle, an additional amount of amino acid, coupling agent, base and HOBT is added to improve the stepwise coupling efficiency. Typically, 99+% coupling efficiency is observed for the first few steps of an average peptide, whereas coupling efficiencies can be much lower as peptide chains are elongated and acquire significant tertiary structure. Doubling coupling can significantly improve the overall yield and purity of the crude product. Even further improvement is seen if peptide chains which fail to add the appropriate amino acid are 'capped' by acetylation, which terminates these chains. The latter procedure avoids the synthesis of nearly perfect peptides, which may have missed a single amino acid and for long peptides, might present purification problems due to the similarity in sequence to the desired full-length peptide. (Doubling coupling was used to insure there was a high level of coupling efficiency; a 5× excess of amino acid, PyBOP, and HOBT was used with a 10× excess of NMM).

Purification of peptide libraries can be performed in two ways; for single step identification (single iterations), purification can be performed by HPLC, where the peptide mixture is loaded in water/0.1% TFA and after a short water/0.1% TFA wash cycle, is eluted with a step gradient of acetonitrile (60% ACN/0.1% TFA) in water/0.1% TFA. Alternatively, for initial drug discovery, where there can be 400 samples, a solid-phase extraction robot can be used to elute the peptides, using a similar strategy to that described above. (HPLC purification on a Vydac C-18 column was used, 5 µ pore size, 10×250 mm).

Example II

Testing Protocols in General

Methods exist for determining the toxicity of novel compounds to potential target microorganisms. For example, growth of pure cultures of a test microorganism can be followed in a microplate reader. Growth rates of cultures can also be determined after the addition of test compounds to the growth media. When a growth rate is slower after the addition of a test compound to the growth media, the compound is said to be an antimicrobial agent. W. F. Broekaert et al., *FEMS Microbiology Letters* 69, 55 (1990).

The key to the successful identification of peptides has been the quantitative assay for measurement of microbial growth. Identification of peptide sequences from SPCL's that inhibit growth of soil-borne plant pathogens was accomplished using a microplate growth assay. Culture volumes and spore or mycelial fragment inoculum densities were optimized for *Fusarium oxysporum* f. lycopersici, *Pythium ultimum, Ceratocystis fagacerum, Rhizoctonia solani,* and *Mycosphaerella fifiensis* growth in microplates. The dry weight of these organisms is directly proportional to their optical density in culture. Thus, growth rates can be determined by measuring increased optical density of a liquid culture through time. Growth rates were determined in the presence and absence of added compositions, such as SPCL's. When growth is inhibited in the presence of these compounds, the compounds are considered to have antimicrobial properties. Similarly, microplate assays have been performed with the microorganisms *Erwinia carotovora* subp. carotovors and *Pseudomonas solanacearum.*

Virtually any soluble compound can be tested for its ability to inhibit microbial growth in this assay, preferably SPCL's or peptides are screened in this manner. Any microorganism that can be grown in liquid culture can be screened with this assay. Although the microorganisms specifically mentioned above are preferred in this invention, animal and human pathogenic organisms such as trypanosomes, Leishmania, *Toxoplasma gondii*, Salmonella, Borrelia, clamydias, *Rickettsia rickettsi*, and plant pathogens such as *Aspergillus flavus, A. niger, A. terreus, Chaetomium globosum, Monilinia fructicola, Penicilium oxalicum,* other Mycosphaerella spp. can also be studied. During the initial screening of the amino acid library, and as described in the further examples below, several peptide mixtures were identified that had strong growth inhibition activity against target pathogens.

When a mixture, such as an SPCL, had antimicrobial activity, peptide species responsible for that activity were identified by synthesis of components of the mixture followed by retesting. Following the initial screen of peptide mixtures which defined the first two positions in the SPCL, those mixtures showing the highest growth inhibition activity were subjected to a successive series of evaluations. In the next round of evaluation, the first three positions of the hexameric sequence were synthesized. Then the XXX-resin was divided into 19 equal portions followed by the addition of one amino acid, $O_3$. This process was followed by the coupling of the previously defined $O_1$ and $O_2$. Thus, 20 peptide mixtures were prepared. In each group the first three residues were defined and the last three residues were random. Each group was then tested in the bioactivity assay as described above. Following this procedure, one additional amino acid was defined at each level of evaluation until each sequence with strong growth inhibition properties was determined. This process permits the complete definition of sequences useful as growth inhibitors of target microorganisms from SPCL libraries.

As the positions are defined, the peptide mixture may show a higher potency or lower $IC_{50}$ (initial concentration of inhibitor for 50% inhibition of growth) for the entire battery of microorganisms tested than the previous less-defined mixture. However, this is not a strict requirement in the present invention because two peptides may have synergistic growth inhibitory effects and their separation may leave purified peptides with lower antimicrobial activity. Alternatively, a peptide may have a synergistic growth inhibiting effect with another compound. Since these as well as presently unknown reasons exist, the inventor chose to not limit selection of peptides to only those that exhibited increasingly lower $IC_{50}$ values for each test organism for each round of synthesis.

Rather, selections were made which generally provided the lowest $IC_{50}$ for the largest number of test organisms. Thus, this approach is distinct from the microorganism-specific experimental designs which maximize the antimicrobial activity of a peptide mixture against a single species of microorganism. For this reason, as will be seen in the Examples to follow, when an additional invariant amino acid residue is added and the resulting peptide mixture is retested against the same battery of test organisms, the $IC_{50}$ may or may not be lowered as it relates to a single species of microorganism since it is the broader inhibitory activity that is initially preferred. Of course, once a collection of peptides is made based upon the broader spectrum of test organisms, refinements may be made as to specific target organisms.

A plant protection assay can also be used to evaluate biological control of fungi causing damping off and root rot. Compositions of the invention are stabilized as described herein (microencapsulation, D-amino acid substitution or terminal end capping, etc.) and then are placed in the soil in contact with or are used to coat the plant, seed, product or the like. A challenge is introduced to the plant, seed or product which consists of an inoculum of the disease causing microorganism. The inoculum may be placed in contact with the plant or added to the plant's resident soil. Alternatively, the inoculum may be injected into the plant's vascular system, particularly where vascular diseases such as those caused by Ceratocystis are being treated. Plant growth is then monitored to determine whether a statistically significant reduction of symptoms such as those seen with damping off or root rot occurs. An effective quantity of the composition is the quantity that results in a significant reduction in visible plant disease symptoms.

Example III

Fungal Growth Inhibition Assay of Fusarium, Rhizoctonia, Pythium and Ceratocystis Growth of Cultures. Cultures of *Fusarium oxysporum* f. sp. lycoperici race 1 (RM-1) [FOLRM-1]; *Rhizoctonia solani* (strain TM-101, anastomosis Group -1) [RS-101]; *Pythium ultimum* (strain LB1, cotton) [PULB1]; and *Ceratocystis fagacearum* (strain BAN 102) [CFBAN102] were routinely maintained on Potato Dextrose Agar (PDA) slants. To obtain microconidia of the *Fusarium oxysporum* f. sp. lycoperici isolate a small portion of an actively growing culture from a PDA plate was transferred to 50 ml of mineral salts medium as described by Esposito and Fletcher (Esposito, R. et al. 1961 *Arch. Biochem. Biophys.* 93:369–376). The culture was incubated with shaking (125 rpm) at 25°. After 96 hrs the fungal slurry consisting of mycelia and microconidia were strained twice through eight layers of sterile cheese cloth to obtain a microconidial suspension. The microconidial suspension was then calibrated with a hemacytometer. Spores of *C. fagacearum* were obtained by growing the culture on PDA plates 25° C. for seven days. The plates were then washed with potato dextrose broth (PDB), strained twice through eight layers of sterile cheese cloth, and the suspension calibrated with a hemacytometer. Microconidia from Fusarium and spores from Ceratocystis were adjusted to 1–5 $\times 10^7$/ml and stored in a 50% solution of glycerol at −80° C. until used. To obtain mycelial fragments of Rhizoctonia, a single sclerotium was inoculated into 50 ml of PDB and incubated at 25° C. with shaking (125 rpm) for 5 days. The mycelial growth was fragmented using a tissue homogenizer with a 0.15 mm clearance between the tube and the piston. The procedure was accomplished on ice to prevent any heating of the sample. The mycelial fragment suspension was calibrated with a hemacytometer. To obtain oospores of Pythium, a PDA plug of the fungus was used to inoculate 25 ml of V-8-cholesterol broth (Ayers, W. A. et al. 1975 Phytopathology 65:1094–1100) dispensed into petri plate and incubated static. After 10 days the mycelial mat was removed, washed twice in sterile water, and macerated in sterile water using a tissue homogenizer as described above. The homogenate was strained twice through eight layers of cheese cloth and the oospore suspensions calibrated with a hemacytometer. All fungal inocula were tested for the absence of contaminating bacteria before their use.

Microplate assay for growth inhibition. To determine the inhibitory affects of the test peptide mixtures, growth of the fungal isolates was determine in their presence. Inhibitory affects to the fungal isolates was accomplished by making a two-fold serial dilution series of an aqueous suspension of the peptide mixtures in PDB in a final volume of 50 μl in a 96-well sterile flat bottom microplate. The fungal inoculum in PDB was then added to each of the wells. Fifty microliters of a suspension containing 6–8$\times 10^4$ Fusarium microconidia/ml was added to the peptide mixture or individual peptide to obtain a final concentration of 3–4$\times 10^3$ microconidia/well. Mycelial fragments of Rhizoctonia were adjusted to 6$\times 10^4$/ml and 50 μl of the suspension was added to the peptide dilution series. Pythium oospores were adjusted to 1$\times 10^5$/ml and 50 μl of the suspension was added to the peptide dilution series. Fifty microliters of a suspension containing 6–8$\times 10^4$ Ceratocystis spores/ml was added to the peptide mixture or individual peptide to obtain a final volume of 100 μl/well and 3–4$\times 10^3$ spores/well. Spores of *Mycosphaerella fijiensis* were grown in soytone-dextrose at pH 6.7. However, better growth can be achieved in pH 5.0–5.5 ranges.

The final concentration of the peptide mixture per well in the two-fold serial dilution series was 2500–1.25 μg/ml or 1250–0.625 μg/ml depending on the initial concentration of the mixture being tested. All plates were incubated static at 25° C. Each plate included three wells that were designated as blanks and 9 wells that monitored the growth of the fungal isolates in the absence of any peptide. Prior to reading the plates were gently shaken to suspend any sedimented growth. Readings were taken at 0, 24, 48 and 70 hrs after inoculation. Growth was monitored by obtaining optical density (OD) readings at 595 nm using an Emax Precision Microplate Reader (Molecular Devices Corp., Menlo Park, Calif.) that was attached to Hewlett-Packard Think-Jet printer. The $IC_{50}$ (the concentration necessary to inhibit 50% of growth) for peptides were calculations based on linear regression analysis of growth dam. Data used to calculate the $IC_{50}$ for each mixture represents a single reading at each concentration for each peptide mixture due to the small amount of sample available for testing. Analyses were carried out in duplicate or triplicate.

Example IV

Peptide-induced Growth Inhibition of Ceratocystis, Rhizoctonia, Fusarium, and Pythium Three rounds of tests were performed using successively defined peptide mixtures derived from the SPCL described above (a D-library). Using the cultural techniques outlined above, cells of the pathogenic fungi *Ceratocystis fagacerum, Rhizoctonia solani, Fusarium oxysporum* and *Pythium ultimum* were tested against the peptide batteries as described.

The $IC_{50}$ (μg/ml) calculated in each instance is that concentration of the test peptide composition that inhibits growth to 50% of that obtained with no peptide added to the growth medium. Calculations of $IC_{50}$ were based upon linear regression analysis of data. In certain instances, $IC_{50}$ values were collected and reported as triplicate independent values using three separate determinations.

The data for each of the four fungal pathogens are tabulated below. In each table, successively defined aliquots of the SPCL are tested. In some instances, the peptide battery first tested was that generally defined as $O_1O_2XXXX$. In others, the first battery tested was $O_1O_2O_3XXX$ (Ceratocystis). In either instance, the next round of peptides tested is defined by an additional fixed residue. The Seq. ID No. is shown for each peptide composition tested.

The shadowed peptide composition in each case is the peptide composition used to define the next round SPCL fraction which was tested. Referring now to Table IV, it can be seen that FRXXXX (Seq. ID No. 1) provided a significantly inhibitory concentration at 557 μg/ml when tested against *Rhizoctonia solani*. Thus, peptides with the FRXXXX were tested in the second round. In the second round, it can be seen that peptides of the general formula FRLXXX (Seq. ID No. 9) demonstrated significant inhibitory activity in three separate experiments of 42, 119 and 94 μg/ml. Subsequently, based upon the indications that FRLXXX (Seq. ID No. 9) peptides were of particular interest, a variety of such peptides were tested and one such peptide composition, FRLKXX (Seq. ID No. 14) was shown in three separate runs to have preferred activity against Rhizoctonia. Similar analyses were applied in each of the four separate fungal groups tested.

It can also be seen by comparison of the Tables (III–VI) summarizing the four fungi tested, that it was possible to utilize the methods of the invention to select peptide compositions with a wide range of anti-fungal characteristics. In each Table and for each succeeding round of testing, the peptide compositions are arranged from top to bottom in increasing $IC_{50}$ values. The topmost peptide compositions in each column were found to be the most inhibitory (lowest $IC_{50}$) for each selected fungus. It can also be seen that in succeeding batteries of peptides tested, alternative peptide compositions gave adequately inhibitory results. These are indicated by shaded boxes in each table. It should be kept in mind that not all peptide compositions tested are represented in the tables below. Only those that exhibited significant $IC_{50}$ values are tabulated. These studies positioned the inventor to conduct studies in which each amino acid residue in the peptide composition was defined.

TABLE III (*Ceratocystis fagacerum*)

| Peptide | IC50 | Peptide | IC50 |
|---|---|---|---|
| FRIXXX ID No. 10 | 43,16,18 | FRLFXX ID No. 18 | 26,16,17 |
| FRWXXX ID No. 12 | 43,18,19 | FRLHXX ID No. 16 | 41,21,20 |
| FRLXXX ID No. 9 | 40,20,21 | FRLKXX ID No. 14 | 47,18,17 |
| FRFXXX ID No. 11 | 48,16,20 | FRLRXX ID No. 15 | 48,32,14 |
| FRMXXX ID No. 13 | 62,32,37 | FRLIXX ID No. 20 | 49,23,23 |
| | | FRLLXX ID No. 21 | 72,21,16 |
| | | FRLTXX ID No. 17 | 78,41,41 |
| | | FRLSXX ID No. 19 | 78,62,66 |
| | | FRLAXX ID No. 22 | 103,75,72 |

TABLE IV (*Rhizoctonia solani*)

| Peptide | IC50 | Peptide | IC50 | Peptide | IC50 |
|---|---|---|---|---|---|
| FRXXXX ID No. 1 | 557 | FRLXXX ID No. 9 | 42,119, 94 | FRLKXX ID No. 14 | 218,65, 79 |
| HFXXXX ID No. 2 | 557 | FRIXXX ID No. 10 | 203,97, 91 | FRLRXX ID No. 15 | 230,152, 124 |
| FKXXXX ID No. 3 | 590 | FRFXXX ID No. 11 | 252,80, 68 | FRLHXX ID No. 16 | 273,167, 152 |
| RQXXXX ID No. 4 | 893 | FRWXXX ID No. 12 | 402,148, 162 | FRLTXX ID No. 17 | 325,165, 156 |
| MRXXXX ID No. 5 | 969 | FRMXXX ID No. 13 | 362,287, 229 | FRLFXX ID No. 18 | 308,131, 214 |
| MHXXXX ID No. 6 | 994 | | | FRLSXX ID No. 19 | 319,284, 134 |
| LKXXXX ID No. 7 | 1099 | | | FRLIXX ID No. 20 | 329,340, 341 |
| LRXXXX ID No. 8 | 1120 | | | FRLLXX ID No. 21 | 379,320, 320 |
| | | | | FRLAXX ID No. 22 | 762,371, 361 |

TABLE V (*Fusarium oxysporum*)

| Peptide | IC50 | Peptide | IC50 | Peptide | IC50 |
|---|---|---|---|---|---|
| HFXXXX ID No. 2 | 309 | FRIXXX ID No. 10 | 173,83, 78 | FRLHXX ID No. 16 | 136,144, 126 |
| MRXXXX ID No. 5 | 487 | FRLXXX ID No. 9 | 311,148, 151 | FRLFXX ID No. 18 | 305,170, 112 |
| MHXXXX ID No. 6 | 531 | FRFXXX ID No. 11 | 327,160, 142 | FRLLXX ID No. 21 | 226,247, 142 |
| FKXXXX ID No. 3 | 597 | FRMXXX ID No. 13 | 356,204, 224 | FRLKXX ID No. 14 | 276,245, 230 |
| LRXXXX ID No. 8 | 724 | FRWXXX ID No. 12 | 570,600, 479 | FRLRXX ID No. 15 | 287,246, 246 |
| FRXXXX ID No. 1 | 875 | | | FRLIXX ID No. 20 | 296,301, 283 |
| RQXXXX ID No. 4 | 992 | | | FRLTXX ID No. 17 | 333,319, 283 |
| LKXXXX ID No. 7 | 1086 | | | FRLSXX ID No. 19 | 726,503, 484 |
| | | | | FRLAXX ID No. 22 | 1472, 792,838 |

TABLE VI (*Pythium ultimum*)

| Peptide | IC50 | Peptide | IC50 | Peptide | IC50 |
|---|---|---|---|---|---|
| RQXXXX ID No. 4 | 132 | FRFXXX ID No. 11 | 85,100, 91 | FRLLXX ID No. 21 | 26,37, 34 |
| LRXXXX ID No. 8 | 347 | FRLXXX ID No. 9 | 138,163, 162 | FRLFXX ID No. 18 | 101,48, 50 |
| MHXXXX ID No. 6 | 414 | FRIXXX ID No. 10 | 193,125, 157 | FRLTXX ID No. 17 | 54,92, 94 |
| MRXXXX ID No. 5 | 440 | FRWXXX ID No. 12 | 273,240, 323 | FRLHXX ID No. 16 | 50,101, 92 |
| FRXXXX ID No. 1 | 492 | FRMXXX ID No. 13 | 326,407, 326 | FRLKXX ID No. 14 | 73,88, 89 |
| FKXXXX ID No. 3 | 505 | | | FRLRXX ID No. 15 | 94,175, 184 |
| LKXXXX ID No. 8 | 530 | | | FRLAXX ID No. 22 | 295,283, 323 |
| HFXXXX ID No. 2 | 679 | | | FRLSXX ID No. 19 | 312,287, 320 |
| | | | | FRLIXX ID No. 20 | 275,322, 323 |

Example V

Peptide-induced Growth Inhibition of Fungi Using Completely Defined Peptides

Fully defined peptide compositions were also tested against the battery of fungi. A similar approach was taken to that described in Example IV above. The peptide compositions were either tri-, tetra- or pentapeptides selected on the basis of the initial screenings accomplished in Example IV above.

Again, linear regression analysis was utilized to generate the tabulated data. For the tripeptide testing, data represented is based upon 72 hr readings for each fungus except Pythium. For Pythium, the data were collected at 48 hrs. For the tetrapeptide dam, all but the Ceratocystis data were collected at 94 hrs. For the pentapeptide data, all data were collected at 72 hrs. In each of Tables VII–IX, "cc" is the correlation coefficient and "n" is the number of data points used in the calculation. Where a D- or an L- analog is tested against one another, the designation "D-" or "L-" precedes the peptide sequence.

In the case of testing of the pentapeptides, by referring to Table IX it can be seen that both D- and L- isomers were tested. In most of the fungi tested, peptide compositions which were composed of D-amino acids were inhibitory at substantially lower concentrations than the L-amino acid analog. However, surprisingly it was found that in certain instances (Ceratocystis), the D- and L-analogs were substantially similar in inhibitory activity.

TABLE VII (Tripeptides)

| Peptide | Fusarium | Rhizoctonia | Ceratocystis | Pythium |
|---|---|---|---|---|
| FRF | 4162 | 816 | 1499 | 1921 |
| ID No. 25 | cc = 0.81 | cc = 0.91 | cc = 0.98 | cc = 0.91 |
|  | n = 5 | n = 6 | n = 4 | n = 5 |
| FRL | 7329 | 1951 | 1250 | 2227 |
| ID No. 26 | cc = 0.97 | cc = 0.88 | cc = 0.96 | cc = 0.99 |
|  | n = 4 | n = 6 | n = 4 | n = 2 |
| FRH | 17,733 | 3949 | 1508 | 2164 |
| ID No. 28 | cc = 0.91 | cc = 0.94 | cc = 0.93 | cc = 0.99 |
|  | n = 4 | n = 4 | n = 4 | n = 3 |

TABLE VIII (Tetrapeptides)

| Peptide | Fusarium | Rhizoctonia | Ceratocystis | Pythium |
|---|---|---|---|---|
| FRLF | 365 | 327 | 70 | 55 |
| ID No. 29 | cc = 0.88 | cc = 0.79 | cc = 0.87 | cc = 0.945 |
|  | n = 4 | n = 3 | n = 4 | n = 3 |
| FRLW | 751 | 328 | 154 | 245 |
| ID No. 30 | cc = 0.90 | cc = 0.74 | cc = 0.86 | cc = 0.95 |
|  | n = 10 | n = 3 | n = 4 | n = 3 |

TABLE IX (Pentapeptides)

| Peptide | Fusarium | Rhizoctonia | Ceratocystis | Pythium |
|---|---|---|---|---|
| D-FRLHF | 31 | 29 | 6.7 | 31 |
| ID No. 31 | s.d. = 0 | s.d. = 4 | s.d. = 1.5 | s.d. = 4 |
| L-FRLHF | 557 | 137 | 12 | 239 |
| ID No. 31 | s.d. = 12 | s.d. = 23 | s.d. = 1 | s.d. = 39 |

Example VI

Growth and Assay for Mycosphaerella

A culture of *Mycosphaerella fijiensis* var difformis ATCC 36054 was routinely maintained on Soytone-Dextrose agar slants. To obtain mycelial fragments of Mycosphaerella, a portion of mycelial growth from a slant was inoculated into 50 ml of Soytone-Dextrose broth (SDB) [adjusted to pH 5.0 with acetic acid] and incubated at 28° C. with shaking (125 rpm) for 6 days.

The mycelial growth was fragmented using a tissue homogenizer with a 0.15 mm clearance between the tube and the piston. The procedure was accomplished on ice to prevent any heating of the sample. The mycelial fragment suspension was calibrated with a hemacytometer. Mycelial fragments of Mycosphaerella were adjusted to $1 \times 10^6$ µg/ml in 1× SDB.

All plates were incubated static at 28° C. Each plate included three wells that were designated as blanks and 9 wells that monitored the growth of the fungus in the absence of any peptide. Prior to reading, the plates were gently shaken to suspend any sedimented growth. Readings were taken at 0, 24, 48, 72, 96, 120 and 144 hrs after inoculation. Growth was monitored by obtaining optical density (OD) readings at 595 nm using a Emax Precision Microplate Reader (Molecular Devices Corp. Menlo Park, Calif.) that was attached to Hewlett-Packart Think-Jet printer. The $IC_{50}$ calculations were based on linear regression analysis of growth data. Data used to calculate the $IC_{50}$ for each mixture represented a triplicate reading at each concentration for each peptide mixture.

*Mycosphaerella fijiensis* var. difformis ATCC 36054 cultures were grown in the presence or absence of the D-amino acid peptide analog of FRLHF (Seq. ID No. 31) in Soytone-Dextrose at pH 6.7 (pH ranges 5.0–5.5 promote better growth). A calculated $IC_{50}$ (µg/ml) of the peptide D-FRLHF (Seq. ID No. 31) of 10.5±2.60 was obtained as the mean of three replicate evaluations. The values were based upon 141 hour readings of growth compared to controls without peptide added. A calculated $IC_{50}$ value of 57±0.0 was obtained as the mean of three replicate evaluations for the peptide L-FRLHF (Seq. ID No. 31).

Example VII

Growth and Assay for Candida.

*Candida albicans* strain BG1 was grown on Tryptic Soy agar (Difco) at 25° C. to obtain chlamydospores. A suspension of the growth was made on Tryptic Soy broth (TSB) and was adjusted to an optical density of 0.10 at 600 nm. The chlamydospore count was determined using a hemacytometer. The peptide or peptide mixture was serially diluted as described above except that TSB was used instead of PDB. Fifty microliters of the chlamydospore suspension was added to the peptide suspension to obtain a final chlamydospore concentration of $1 \times 10^6$ per well. The final concentration of the peptide or peptide mixture per well in the two-fold serial dilution series in a final volume of 50 µl, in a 96-well sterile flat bottom microplate, was 2500–1.255 µg/ml or 1250–0.625 µg/ml depending on the initial concentration of the peptide or peptide mixture being tested.

The microtiter plates were incubated at 37° C. on a rotary platform shaker at 200 RPM. Each plate included three wells that were designated as blanks and 9 wells that monitored the growth of the fungal isolate in the absence of any peptide.

Prior to reading, the plates were gently shaken to suspend any sedimented growth. Readings were taken at 0 hr and hourly for 8 hrs thereafter. Growth was monitored by obtaining optical density (OD) readings at 595 nm using a Emax Precision Microplate Reader (Molecular Devices Corp. Menlo Park, Calif.) that was attached to a Hewlett-Packard Think-Jet printer. The $IC_{50}$ for peptides were calculated using linear regression analysis of growth data.

Mycelia dry weight and optical density correlation. The fungal isolates were inoculated as described above in the absence of any inhibitory compounds. The OD readings were taken over a 96 hr period with thirty wells collected at each of the time periods. The samples were collected by filtration (10/filter) through preweighed glass filters (0.45 microns). The filters were dried in a vacuum oven at 70° C. to constant weight and the tared weight subtracted from the sample-filter weight to determine mycelia mass dry weight.

Example VIII

Peptide-induced Growth Inhibition of Yeasts

Similar studies were carried out on yeast. The data reported in Table X are based on log regression analysis of the data. The data were based on 6 hr readings of cultures incubated at 37° C.

Referring now to Table X, it can be seen that certain of the variable peptide compositions of the invention were tested against the yeast, Candida albicans. Additionally, certain fully defined peptides of the invention comprising three and four residues were tested. Where an L-analog is tested instead of a D-analog, the designation "L-" precedes the peptide sequence.

TABLE X (Candida albicans)

| Peptide | IC$_{50}$ | Peptide | IC$_{50}$ |
|---|---|---|---|
| FRLXXX ID No. 9 | 89 cc = .99 n = 4 | FRLHXX ID No. 16 | 497 cc = .98 n = 5 |
| FRIXXX ID No. 10 | 106 cc = .99 n = 4 | FRLWXX ID No. 23 | 519 cc = .92 n = 5 |
| FRFXXX ID No. 11 | 578 cc = .72 n = 8 | FRLF ID No. 29 | 637 cc = .99 n = 7 |
| FRMXXX ID No. 13 | 611 cc = .81 n = 6 | FRLW ID No. 30 | 641 cc = .99 n = 5 |
| FRWXXX ID No. 12 | 616 cc = .75 n = 6 | L-FRLF ID No. 29 | 946 cc = .88 n = 4 |
| FRLLXX ID No. 21 | 97 cc = .97 n = 4 | FRL ID No. 26 | 1550 cc = .77 n = 4 |
| FRLFXX ID No. 18 | 108 cc = .97 n = 3 | FRW ID No. 27 | 1837 cc = .99 n = 4 |
| FRLIXX ID No. 20 | 159 cc = .79 n = 3 | FRH ID No. 28 | 1889 cc = .98 n = 5 |
| FRLMXX ID No. 24 | 210 cc = .99 n = 3 | FRF ID No. 25 | 1994 cc = .98 n = 6 |
| FRLRXX ID No. 15 | 409 cc = .96 n = 4 | | |

Example IX

Animal Fungal Diseases (Pythium, Candida)

It is anticipated that the present invention will also find use in treating animal infections. Table XI below shows a variety of fungal diseases of animals and man amenable to the compositions and methods of the invention. A pharmaceutical composition useful for treating bacterial or fungal infections is provided by the present invention. This pharmaceutical composition comprises an effective amount of the antimicrobial agent and a pharmaceutically acceptable carrier. Certain of the disease organisms listed here were tested with the peptide compositions detailed herein. Pharmaceutically acceptable carriers are known in the art and are disclosed in The Pharmacopeia of the United States and the National Formulary in which the peptides of the invention may be delivered.

TABLE XI

| FUNGUS | TARGET |
|---|---|
| Systemic: | |
| *Blastomyces dermatitidis* | man, dogs |
| *Coccidioides immitis* | man, dog, cattle, horse, cat, sheep, rodents (several attempts at a vaccine have been made) |
| *Histophasma capsulatum* | man, dog, cat, horse |
| *Pythium* spp. | dogs, horses |
| *Zygomycetes* spp. | swine, goat, cattle, deer, horses, dogs, cats |
| *Rhinosporidum seeberg* | dogs, horses, man |
| *Sporothrix schenckii* | cat, dog, horse, man |
| Dermatocytes: | |
| *Microsporum canis* | cat, dog, horse, man |
| *Microsporum distortum* | dog |
| *Microsporum gypseum* | everything |
| *Microsporum nanum* | swine |
| *Trichophyton mentagrophytes* | dog, cat, cattle, horse, man |
| *Trichophyton equinum* | horse |
| *Trichophyton verrucosum* | cattle, man (there is a vaccine in Europe) |
| *Trichophyton gallinae* | birds |
| Human Systemic Fungal | Incidence (cases per year) |
| Nosocomial Infections | |
| Candida spp. (Species listed in descending frequency of infection causation) | 202,000 |
| albicans | |
| topicalis | |
| parapsilosis | |
| krusei | |
| pseudotropicalis | |
| stellatoidea | |
| guilliermondii | |
| lusitaniae | |
| rugosa | |
| Aspergillus spp. | 43,000 |
| Torulopsis glabrata | 18,000 |
| Zygomycetes | 7,000 |

Depending on the specific application contemplated, the pharmaceutical composition provided by the subject invention may be formulated as a solution, suspension, parental preparation, ointment, cream, lotion, spray, powder, or tablet capsule. Parental preparations may include a vehicle such as specially distilled, pyrogen-free water, phosphate buffer, or normal saline. Ointments, creams, lotions and sprays may include a carrier such as vegetable or mineral oil, white petrolatum, or a high molecular weight alcohol, i.e., greater than C12. Tablets or capsules may include diluents, (e.g., lactose), binders, lubricants (e.g., stearic acid) and a disintegrator (e.g., corn starch).

Also provided is a method for treating a subject having a fungal infection which comprises administering to the subject an effective bacterial or fungal killing amount of the pharmaceutical composition of the present invention. Modes of administration are well recognized in the art for treatment or prevention of bacterial or fungal infections of the mucosa. Creams, suppositories or solutions which contain the active ingredient may be placed in contact with the infected area. When the infection is external, a cream may be massaged into the infected and surrounding area twice daily until after the infection has been eradicated. Where intravaginal use is required, approximately 5 grams of the cream should be injected high into the vaginal vault using a conventional applicator. This treatment should be repeated twice a day until the infection has been eradicated. Alternatively, vaginal suppositories may be inserted high into the vaginal vault once or twice daily and treatment continued until the infection has been eradicated.

A conventional denture adhesive paste may be formulated containing an effective amount of antimicrobial agent. Typical concentrations will range from 0.0125% to 1.5% by weight of antimicrobial agent per 100 grams of paste. Approximately 2 grams of paste is applied in the conventional manner to the contact surface of the denture prior to insertion into the mouth. Such application should be made after overnight soaking in the denture cleanser. Denture cleansers may be formulated by the addition of an effective amount of the antimicrobial agent to a tablet of approximately 3 to 3.5 grams. Such a tablet is dissolved in water yielding an antimicrobial solution for cleansing dentures. In the preferred mode of use, the denture after removal from the patient's mouth, is soaked in this cleanser for from about 8 to about 12 hours. If desired, in place of utilizing a denture cement, a denture adhesive powder can also be formulated with the antimicrobial agents of this invention.

A mouth spray containing an effective amount of the active agent may also be formulated. This material may be sprayed as an antimicrobial agent in 0.25 to 0.5 ml. aliquots onto the tooth and gingiva surfaces of each quadrant between 1 and 3 times per day. In the case of denture wearers, the spray may be utilized directly on the denture surface prior to daily insertion of the denture. If desired, a mouthwash formulation may be provided containing an effective amount of the antimicrobial agent. Pharmaceutical composition is also provided for therapeutic treatment of fungal infections. See U.S. Pat. No. 5,126,257, pg. 5.

The antimicrobial agents may be employed to provide dosages of from 1 to 500 mg per kilogram of host weight, when administered systemically. Active agents can be formulated in phosphate buffered saline solution. Aerosol spray inhalants are also known via which the antimicrobial peptide compositions of the invention may be introduced.

Example X

Obligate Parasitic Organisms.

In certain instances, it may be more desirable to conduct the inhibition assays directly on certain susceptible host organisms where such microorganisms cannot grow independent of the host organism or where independent growth of the microorganism from the host is otherwise problematic. For example, powdery mildew of roses is caused by the obligate parasite *Sphaerothecia pannosa* f. sp. rosae. In such instances, it will be necessary to test inhibition of the peptide or peptide mixture on infected host plants.

EXAMPLE XI

Postharvest Fruit Wounding Studies

In other instances, it may be desirable to test the effectiveness of the peptide compositions of the invention directly on harvested produce such as fruit. Janisiewicz, et al. 1991, describes a postharvest test for control of blue mold and gray mold of apples and pears by dip treatment with pyrrolnitrin which is exemplary. See, article by the same authors at *Plant Disease* 75: 490–494 (1991). Pathogens of interest will be isolated and preserved as described above.

Golden Delicious apples will be harvested and maintained with a minimal spray regime. The fruit may be stored at 1°±1° C. and 95±2% relative humidity (RH) for at least 2 months before use. The fruit used in the tests will be selected for uniformity in size and ripeness. Similarly, Bosc pears will be harvested and stored under the same conditions and used within 2 months of harvest. Firmness of the apples and pears will be tested prior to inoculating with fungi and should have a firmness of approximately 11 (apples) and 14 (pears) lbs. of force as determined by Effegi pressure tests.

Fruit will be wounded by one of three methods. Cut wounds will be made by cutting a 3-mm-square incision 3 mm deep with a sharp instrument and removing the tissue. Two such wounds will be made approximately 2 cm apart on each fruit. Puncture wounds will be made with two 6.1-mm-diameter nails 2 cm apart and protruding 4 mm front a wooden block. "Bruise" wounds will be made by pressing two screw heads (1 cm in diameter) against the fruit surface to a depth of 2–3 mm, breaking the skin of the fruit. The screw heads will be mounted on a wooden block 2 cm apart. All wounds will be made about halfway along the line between the calyx and stem end.

Fruit will be dipped in suspensions containing the test organism alone or mixed with various concentrations of the peptide composition to be tested. Wounded apple or pear fruit (two wounds per fruit) will be dipped in the suspensions for 2 min with occasional agitation. The fruit will then be placed on polystyrene fruit tray-packs with the wounded face up in 1-bushel fruit boxes with polyethylene liners. Fruit from each treatment will be placed on separate trays in separate boxes. Five fruit will be used per treatment, and each treatment will be repeated three times. The boxes will be placed in storage as randomized blocks.

One set of fruit so treated will be stored at 24° C. and 95±2% RH for 7 days, and the other set will be stored at 2° C. for 30 days. Storage at 24° C. is designed to maintain or establish optimal conditions for development of the fungal diseases, and lengths of storage periods will be selected to make it possible to measure lesions before fruits are entirely rotted. At the end of the storage period, diameters of lesions will be measured perpendicular to the axis connecting the two wounds.

Example XII

Phytotoxicity/Mutagenicity Determinations

Phytotoxicity studies will be conducted by monitoring the growth of duckweed (*Lemna minor*) and the germination of rice seed (*Oryzae sativa*). Common duckweed phytotoxicity tests are simple, sensitive, and cost effective. Axenic *L. minor* will be grown in flasks using the medium of Bowker as described by Caux (Caux, P. Y., et al. 1988. *Environmental Toxicology and Chemistry* 7:671–676). A clonal population will be obtained by vegetative multiplication of a single frond inoculum. The individual peptides will be added to the assay medium, and the plants will be monitored for increase in biomass and photosynthetic dysfunction (Caux, P. Y., et al. 1988. *Environmental Toxicology and Chemistry* 7:671–676) for a 14-day period. Rice is an economically important crop and is a recommended species for toxicity testing. (Wang, W. 1991. *Environmental Toxicology and Chemistry* 10:1173–1177). Conditions for testing will be those described by Wang (Wang, W. 1991. *Environmental Toxicology and Chemistry* 10:1173–1177). To evaluate potential genotoxicity, the peptides of interest will be evaluated using the Salmonella/microsome assay (Maron, D. M., and B. N. Ames. 1983. *Mutat. Res.*:173–215) and the Microscreen Prophage-induction assay (Rossman, T. G., et al. 1984. *Environ. Mutagen.* 6:59–69). Hemolytic activity will be assessed by the method of Zasloff (Zasloff, M. 1987. *Proc. Natl. Acad. Sci.* USA 84:5449–5453).

Example XIII

Stabilizing Peptides

A variety of modifications can be made to the peptides as long as antimicrobial activity is retained. Some modifications may be used to increase the intrinsic antimicrobial potence of the peptide. Other modifications may facilitate handling of the peptide. Peptide functional groups that may typically be modified include hydroxyl, amino, guanidinium, carboxyl, amide, phenol, imidazol rings or sulfhydryl. Typical reactions of these groups include but are not limited to acetylation of hydroxyl groups by alkyl halides. Carboxyl groups may be esterified, amidated or reduced to alcohols. Carbodiimides or other catalysts may be used to catalyze the amidation of carboxyl groups. The amide groups of asparagine or glutamine may be deamidated under acidic or basic conditions. Acylation, alkylation, arylation or amidation reactions readily occur with amino groups such as the primary amino group of the peptide or the amino group of lysine residues. The phenolic group of tyrosine can be halogenated or nitrated. Examples where solubility of a peptide could be decreased include acylating charged lysine residues or acetylating the carboxyl groups of aspartic and glutamic acids. Peptides may be conjugated to soluble or insoluble carrier molecules to modify their solubility properties as needed and to increase the local concentrations of peptides in their target areas. The peptide compositions of the invention may also be injected into the vascular system of a plant. Examples of soluble carrier molecules include polymers of polyethyleneglycol and polyvinylpyrrolidone. Examples of insoluble polymers include sand or other silicates or polystyrene, cellulose, or the like. Peptides may also be micro-encapsulated to enhance their stability during seed, soil, or plant application. Typically, polyester microspheres are used to encapsulate and stabilize the peptides.

Example XIV

Large-Scale Peptide Synthesis

Large-scale (up to 60 kg) peptide synthesis in solution or solid-phase will be accomplished once particular peptide compositions are selected to be used en masse. This synthesis requires a careful selection of protecting groups and condensing methods. All starting materials and reagents can be obtained with good purity from chemical suppliers such as Sigma Chemical Co. or Aldrich Chemical Co. The racemization of amino acid building blocks under coupling conditions can be greatly suppressed or eliminated by the use of new generation reagents, i.e. HOBt, HOAt, HBTU or HATU. Even the solid-phase methodology is presently suitably developed to manufacture pharmaceutical peptides at multiples of 1–10 kg/year.

Large-scale synthesis of peptides in solution. The solution-phase synthesis allows easy planning with respect to group protection strategy, fragment selection and methods of fragment coupling to minimize racemization. The intermediates can sometimes be isolated simply by crystallization techniques, which may eliminate the need for purification by column chromatography and therefore improve the scale-up potential. The quality of simultaneously-produced fragments can be easily controlled at each step.

Large scale solid-phase synthesis of peptides. The cost of the more advanced polymers for solid-phase synthesis is usually high. Some of the supports are not available in bulk. However, their properties play an important role in the accessibility of anchored peptide and release of the peptide from the resin in a fully protected, deprotected or modified form. The transition from laboratory to manufacturing scale of solid-phase peptide synthesis (SPPS) is clearly advantageous due to the fact that the entire synthetic process could be easily automated, and the efficiency of the synthetic steps could be monitored and optimized. The production scale activating processes are well known and environmentally harmless. In addition, SPPS allows direct recovery and recycling of excess of amino acid building blocks from the waste filtrates at production scale.

The following references are incorporated specifically by reference herein: Boris Gorup, "Production of large-scale peptides in solution." *Biochem. Soc. Trans.*, 18(6), 1299–306; Christian Birr, "The transition to solid-phase production of pharmaceutical peptides." *Biochem. Soc. Trans.*, 18(6), 1313–16; and Paul Lloyd-Williams, Fernando Albericio and Ernest Giralt, "Convergent solid-phase peptide synthesis." *Tetrahedron* 49(48), 11065–11133. Where large-scale syntheses are to be attempted of the peptide compositions of the invention, the methods and materials recited in these references should be followed.

Of course, where it has been determined that an L-amino acid peptide is sufficiently inhibitory (either with or without stabilization), it may be possible to use recombinant DNA expression according to techniques known well to those of skill in the art to produce such peptides in large scale amounts. Where recombinant peptides are produced and where stability of such peptides is desired, the peptide may be protected from attack at each terminus by covalently linking D-amino acids to one or the other or both termini using techniques known to those of skill in the art of peptide chemistry.

Example XV

Microspheres Encapsulation of Peptides

Various methods of microsphere preparation may be used depending upon the hydrophilic or hydrophobic nature of the peptide composition to be encapsulated. Wang, H. T., et al. 1991, "Influence of formulation methods on the in vitro controlled release of protein from poly(ester) microspheres," *J. of Controlled Release* 17:23–25 is specifically incorporated herein to the extent that it provides methods and materials not addressed herein.

(1) o/o Emulsion method. A TTA-60 titration assembly (Radiometer, Copenhagen, Denmark) will be used in this method for efficient stirring. Poly(DL-lactide/glycolide, 50:50, Dupont) (0.5 g) will be dissolved in methylene chloride (3.3 ml). Spray-dried peptides (25 mg) may then be dispersed in this solution by applying sonification for 30 s in an ultrasonic cleaner (Branson 3200, Branson Cleaning Company, Shelton, Conn.). This suspension may then be passed dropwise through a syringe with a 220 gauge needle into a well-stirred emulsion containing silicone oil (20–30 ml), $CH_2Cl_2$ (30–40 ml) and Span 85 (2 ml). Petroleum ether (30 ) may then be added dropwise into the above dispersion. Stirring may then be continued for 2 hr. Microspheres produced in this manner will then be filtered, washed with petroleum ether and dried in a vacuum for 72 hr.

(2) o/w Emulsion method. An ultrasonified suspension of spray-dried peptide (25 mg), poly(DL-lactide/glycolide, 50:50) (Dupont or Birmingham Polymers) (0.5 g) and $CH_2CL_2$ (2 ml) will be emulsified with an aqueous solution (50 ml) containing sodium oleate (0.2 g) in a TTA-60 titration assembly for 5 min. The methylene chloride will be removed with a rotary-evaporator (120 rpm) at 360 Torr (1 h at 22° C.), 160 Torr (0.5 h at 22° C) and 160 Torr and 40° C. (1 h). The microspheres obtained will be filtered, washed with water and vacuum dried at room temperature.

(3) (w/o)/w Emulsion method. A solution of peptide (2.6 mg) in distilled water (100 μl) will be emulsified with methylene chloride solution (0.5 g/2 ml) of poly(DL-lactide/glycolide, 50:50 Henley Chemical, RG503) through the use of a probe sonicator (Branson, Danbury, Conn.) at 125 W and 40% duty cycle, pulsed mode. This emulsion (w/o) will be emulsified in an aqueous solution (50 ml, 35° C.) containing 0.1% polyvinyl alcohol with a homogenizer (5000 rpm, ESGE Handmixer M122, Biospec Products, Bartlesville, Okla.) for 5 min. Methylene chloride will be removed from the resulting (w/o)/w emulsion on a rotary-evaporator at 300 Torr and 34° C. (120 rpm) for 1 h. The microspheres obtained will be filtered, washed with water and either vacuum dried at room temperature or lyophilized (Consol 4.5, Virtis Co., Gardiner, N.Y.).

Polymer molecular weights may be determined by gel permeation chromatography. Particle sizes of microspheres may be determined by scanning electron microscopy (SEM, Hitachi S-570, Tokyo, Japan).

In vitro peptide release studies may also be performed. Microspheres (200 mg) will be suspended in pH 7.2 phosphate-buffered saline (PBS) (2.5 ml) and agitated at 37° C. and 100 rpm in an environmental incubator shaker (G-24, New Brunswick Scientific Co., Edison, N.J.). At specific sampling times (each day for the first 4 days and every other day for the remainder of the study) the buffer solution will be completely removed and replaced with fresh PBS. The peptide content of the PBS will be measured using the Bradford method or other suitable quantitative assay.

Other methods of microencapsulation are known which may find usefulness in certain instances. See, e.g., U.S. Pat. No. 4,324,683.

Example XVI

Seed Treatment

A method for protecting seeds is also disclosed. The process of coating seeds with an antimicrobial compound is well known to those skilled in the art. Any conventional method that does not destroy the active ingredient is adequate for the purposes of this invention. An easy and preferred method is to suspend or dissolve the active ingredient in 1.0–1.5 % aqueous methyl cellulose. The seed to be protected is added to the suspension and is mixed vigorously with it to coat the surface of the seed with the suspension. The seed is then air dried. The seed is protected from fungal infections upon germination because the coating material places the active ingredient in the immediate vicinity of the seed.

Effective concentrations of the active ingredient are determined by mixing varied amounts of the active ingredient into the liquid coating mixture and coating batches of seeds. The seeds are then planted in soil and challenged with disease microorganisms. The germination rate of the seeds is determined and a minimum concentration of active ingredient is determined when it yields statistically improved germination rates. Seedling survival and general plant survival rates can also be determined. Higher concentrations of the antimicrobial agent may be used if they are shown to increase seedling or plant survival or increase plant yields.

Other methods of controlling agricultural fungus infections may be used. Microorganisms can be contacted directly with an effective amount of an active ingredient composition of this invention, typically dissolved in the appropriate carrier. Examples of appropriate carriers are known in the art and may comprise phosphate buffer or phosphate buffered saline at physiological pH.

Seed treatment by means of application of materials either chemical, biological, or a combination, to seed in order to protect from attack by soil borne pathogens and insects, may be typically accomplished using two common application methods.

(1) Commercially coating by seed companies. Commercial treaters will normally create a slurry of the peptide material in water and apply the slurry as a spray to the seed. The seed will then be dried and bagged for sale.

(2) A hopper box method may also be used. The peptide material is applied by the grower before planting. The material is sprinkled as a dry powder over the top of the hopper box. Typically, half the seed is placed in the hopper box, half the fungicide, then the rest of the seed, and finally the rest of the fungicide.

REFERENCES CITED

The following references to the extent that they provide procedural details supplementary to those set forth herein, are specifically incorporated herein by reference.

Caux, P. Y., P. Weinberger, and D. B. Carlisle. 1988. A physiological study of the effects of triton surfactants on *Lemna minor* L. Environmental Toxicology and Chemistry 7:671–676.

Cull, M. G., J. F. Miller, and P. J. Schatz. 1992. Screening for receptor ligands using large libraries of peptides linked to the C terminus of the lac repressor. Proc. Natl. Acad. Sci. USA 89:1865–1869.

Fiedler, H. P., R. Kurth, J. Langharig, J. Delzer, and H. Zahner. 1982. Nikomycins: microbial inhibitors of chitin synthase. J. Chem. Technol. Biotechnol. 32:271–280.

Furka, A., F. Sebastyen, M. Asgedom, and G. Dibo. 1991. General method for rapid synthesis of multicomponent peptide mixtures. Int. J. Pept. Protein Res. 37:487–493.

Gramsch, C., T. Meo, G. Riethmuller, and A. Herz. 1983. Binding characteristics of a monoclonal β-endorphin antibody recognizing the N-terminus of opioid peptides. J. Neurochem. 40:1220–1226.

Houghten, R. A., C. Pinilla, S. E. Blondelle, J. R. Appel, C. T. Dooley, and J. H. Cuervo. 1991. Generation and use of synthetic peptide combinatorial libraries for basic research and drug discovery. Nature 354:84–86.

Houghten, R. A., J. R. Appel, S. E. Blondelle, J. H. Cuervo, C. T. Dooley, and C. Pinilla. 1992. The use of synthetic peptide combination libraries for the identification of bioactive peptides. BioTechniques 13:412–421.

Houghten, R. A., Blondelle, S. E., Cuervo, J. H., in *Innovations and Perspectives in Solid Phase Synthesis*. Canterbury; Epton, R., Ed., Solid Phase Conference Coordination, Ltd.: Canterbury, 1992.

Isono, K. and S. Suzuki. 1979. The polyoxins: pyrimidine nucleoside peptide antibiotics inhibiting fungal cell wall biosynthesis. Heterocycles 13:333–351.

Lerner, R. A. 1982. tapping the immunological repertoire to produce antibodies of predetermined specificity. Nature 299:592–596.

Maron, D. M., and B. N. Ames. 1983. Revised methods for the Salmonella mutagenicity test. Mutat. Res.: 173–215.

Pinilla, C., J. R. Appel, and R. A. Houghten. 1992. Synthetic peptide combinatorial libraries: the screening of tens of millions of peptides for basic research and drug discovery. in *Vaccines* 92; Brown, F., Chanock, R. M., Ginsberg, H. S., Lerner, R. A., Eds. Cold Spring Harbor Laboratory Press, Cold Spring Harbor, 1992 p. 25 et seq.

Rossman, T. G., M. Molina, and L. W. Meyer. 1984. the genetic toxicology of metal compounds. I. Induction of lambda prophage in *E. coli* WP2, Environ. Mutagen. 6:59–69.

Wang, W. 1991. Ammonia toxicity to macrophytes (common duckweeds and rice) using static and renewal methods. Environmental Toxicology and Chemistry 10:1173–1177.

Zasloff, M. 1987. Magainins, a class of antimicrobial peptides from Xenopus skin: Isolation, characterization of two active forms, and partial cDNA sequence of precursor. Proc. Natl. Acad. Sci. USA 84:5449–5453.

The present invention has been described in terms of particular embodiments found or proposed to comprise preferred modes for the practice of the invention. It will be appreciated by those of skill in the art that, in light of the present disclosure, numerous modifications and changes can be made in the particular embodiments exemplified without departing from the intended scope of the invention. For example, it is of course possible that once discovered using the methods and compositions of the present invention, that a given peptide or peptides may be produced recombinantly in the organism which is susceptible to a fungal infection treatable with the same peptides. Thus, if an L-amino acid pentapeptide such as one of the preferred peptide compositions of the invention, Seq. ID. No. 31 (FRLHF), were encoded in a DNA fragment, that fragment then could be incorporated into the genome of a susceptible plant. The numbers of copies of such a peptide as well as the expression level could be modified to maximize the protection provided. By expressing the peptide in a manner which exposes the peptide to the fungal pathogen cell, control may be achieved (see, e.g., published PCT application PCT/US93/ 07882). It is also likely that as the inventor generates greater numbers of antifungal peptides, that preferred mixtures of such peptides will be possible and may be selected for specific pathogens. Thus, for instance, the combination of Seq. ID No. 25 (FRF) and Seq. ID No. 29 (FLRF) are shown herein to have antifungal activity toward the pathogen Fusarium and may be combined and tested for greater combined activity. All such modifications are intended to be included within the scope of the appended claims.

What is claimed is:

1. An antibiotic composition comprising at least one of the peptides having the sequence defined in Seq. ID Nos. 2–7, 9–11, 13–28 and 31.

2. The antibiotic of claim 1 wherein at least one of the amino acids comprising said peptide is a D-stereoisomer.

3. The antibiotic of claim 1 further comprising a carrier.

4. The antibiotic of claim 3 wherein said carrier further comprises a microsphere.

5. The antibiotic of claim 1, capable of inhibiting growth of a fungus.

6. The antibiotic of claim 5 wherein said fungus is selected from the group of fungi consisting of Fusarium, Rhizoctonia, Ceratocystis, Pythium, Mycosphaerella and Candida.

7. An antibiotic mixture composition comprising an equimolar ratio of peptides of a synthetic peptide combinatorial library having the sequence of one of the peptides of Seq. ID Nos. 2–7, 9–11 and 13–24.

8. The antibiotic mixture of claim 7, capable of inhibiting growth of a fungus.

9. The antibiotic mixture of claim 8 wherein said fungus is selected from the group of fungi consisting of Fusarium, Rhizoctonia, Ceratocystis, Pythium, Mycosphaerella and Candida.

10. The antibiotic mixture of claim 7 wherein at least one of the amino acids comprising said peptide is a D-stereoisomer.

11. An antibiotic composition consisting essentially of one of the peptides of Seq. ID Nos. 25–28 and 31.

12. The antibiotic of claim 11, capable of inhibitory growth of a fungus.

13. The antibiotic of claim 12 wherein said fungus is selected from the group of fungi consisting of Fusarium, Rhizoctonia, Ceratocystis, Pythium, Mycosphaerella and Candida.

14. An antibiotic composition consisting essentially of one of the peptides of Seq. ID Nos. 25–28 and 31, which antibiotic inhibits growth of a fungal cell, which fungal cell is selected from the group of fungi consisting of Fusarium, Rhizoctonia, Ceratocystis, Pythium, Mycosphaerella and Candida.

15. The antibiotic of claim 14 wherein at least one of the amino acids comprising said peptide is a D-stereoisomer.

16. An antibiotic composition consisting essentially of the peptide of Seq. ID No. 31, which antibiotic inhibits growth of Mycosphaerella fijiensis when applied in an effective amount to a plant from the family Musaceae.

17. A method for inhibiting growth of a fungal cell consisting essentially of contacting said cell with at least one of the peptides of Seq. ID Nos. 2–7, 9–11 and 13–28.

18. The process of claim 17 wherein said fungal cell is selected from the group of fungi consisting of Fusarium, Rhizoctonia, Ceratocystis, Pythium, Mycosphaerella and Candida.

19. The process of claim 18 wherein said fungus is a pathogen of a plant.

20. The process of claim 19 wherein said plant is a seed.

21. The process of claim 19 wherein said plant is a fruiting body.

22. The process of claim 18 wherein said fungus is a pathogen of an animal.

23. The process of claim 22 wherein said animal is a human.

24. A process for inhibiting the growth of Mycosphaerella fijiensis on a plant of family Musaceae consisting essentially of contacting said plant or a part derived therefrom with an effective amount of the peptide of Seq. ID No. 31.

25. An antibiotic composition consisting essentially of one of the peptides of Seq. ID Nos. 25–28 and 25, which antibiotic inhibits growth of a fungal cell, which fungal cell is selected from the group of fungi consisting of Fusarium, Rhizoctonia, Ceratocystis, Pythium, Mycosphaerella and Candida.

26. A method for inhibiting growth of a fungal cell consisting essentially of contacting said cell with at least one of the peptides of Seq. ID Nos. 2–7, 9–11, 13–28 and 25, wherein said fungal cell is selected from the group of fungi consisting of Fusarium, Rhizoctonia, Ceratocystis, Pythium, Mycosphaerella and Candida, and wherein said fungus is a pathogen of a plant.

27. A method for inhibiting growth of a fungal cell consisting essentially of contacting said cell with at least one of the peptides of Seq. ID Nos. 2–7, 9–11, 13–28 and 25, wherein said fungal cell is selected from the group of fungi consisting of Fusarium, Rhizoctonia, Ceratocystis, Pythium, Mycosphaerella and Candida, wherein said fungus is a pathogen of a plant, and wherein said plant is a seed.

28. A method for inhibiting growth of a fungal cell consisting essentially of contacting said cell with at least one of the peptides of Seq. ID Nos. 2–7, 9–11, 13–28 and 25, wherein said fungal cell is selected from the group of fungi consisting of Fusarium, Rhizoctonia, Ceratocystis, Pythium, Mycosphaerella and Candida, wherein said fungus is a pathogen of a plant, and wherein said plant is a fruit.

* * * * *

UNITED STATES PATENT AND TRADEMARK OFFICE
CERTIFICATE OF CORRECTION

PATENT NO : 5,602,097
DATED : Feb. 11, 1997
INVENTOR(S) : David L. Edwards

It is certified that error appears in the above-identified patent and that said Letters Patent is hereby corrected as shown below:

Column 40, line 61, delete "25" and insert --31-- in place thereof.

Column 41, line 1, delete "25" and insert --31-- in place thereof.

Column 41, line 8, delete "25" and insert --31-- in place thereof.

Column 42, line 5, delete "25" and insert --31-- in place thereof.

Signed and Sealed this

Seventh Day of July, 1998

Attest:

BRUCE LEHMAN

*Attesting Officer*        *Commissioner of Patents and Trademarks*